United States Patent [19]

Baxter et al.

[11] Patent Number: 4,486,354
[45] Date of Patent: Dec. 4, 1984

[54] SUBSTITUTED AROMATIC COMPOUNDS

[76] Inventors: Martin G. Baxter, 34 Whitehead Close, Wilmington, Dartford, Kent; Albert R. Elphick, 51 Baring Rd., Lee, London, SE. 12; Alistair A. Miller, 91 Elmshurst Gardens, Tonbridge, Kent; David A. Sawyer, 60 Bourne Vale, Hayes, Kent, all of England

[21] Appl. No.: 308,805

[22] Filed: Oct. 5, 1981

Related U.S. Application Data

[63] Continuation of Ser. No. 154,198, May 29, 1980, abandoned.

[30] Foreign Application Priority Data

Jun. 1, 1979 [GB] United Kingdom ............... 7919257

[51] Int. Cl.$^3$ ............................................. C07C 121/84
[52] U.S. Cl. ................................. 260/465 E; 544/182; 424/249
[58] Field of Search ................................. 260/465 E

[56] References Cited

U.S. PATENT DOCUMENTS 2,952,677  9/1960  Birtwell et al. ...................... 260/240
3,637,688  1/1972  Rees et al. ................. 260/465 E UX
4,311,701  1/1982  Roth et al. ........................... 424/249

FOREIGN PATENT DOCUMENTS 190941   9/1956  Austria .
759014  10/1956  United Kingdom .
1223491  2/1971  United Kingdom .
1318645  5/1973  United Kingdom .

OTHER PUBLICATIONS

Rees, et al., J. of Med. Chem., 15, (1972), pp. 859–861.

Primary Examiner—Joseph Paul Brust
Attorney, Agent, or Firm—Donald Brown

[57] ABSTRACT

The present invention provides compounds of the formula (III):

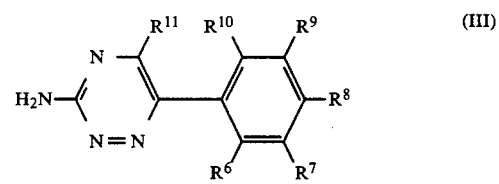

or an acid addition salt thereof, wherein $R^6$ is chlorine, bromine, iodine, $C_{1-4}$ alkyl or trifluoromethyl, or $R^6$ and $R^7$ form a —CH=CH—CH=CH—group optionally substituted by a halogen atom or a $C_{1-4}$ alkyl or trifluoromethyl group, $R^8$ is hydrogen, bromine, iodine, $C_{1-4}$ alkyl or trifluoromethyl, $R^9$ is hydrogen, halogen, $C_{1-4}$ alkyl or trifluoromethyl, $R^{10}$ is hydrogen, methyl or fluorine and $R^{11}$ is amino, $C_{1-10}$ acylamino or di-substituted aminomethyleneamino provided that, at most, only two of $R^7$–$R^{10}$ are other than hydrogen and that $R^7$–$R^{10}$ are not all hydrogen when $R^6$ is chlorine. Also provided are pharmaceutical compositions containing compounds of the formula (III), the first medical use of compounds of the formula (III), a process for preparing such compounds and intermediates through which this process proceeds.

3 Claims, No Drawings

SUBSTITUTED AROMATIC COMPOUNDS

This is a continuation of application Ser. No. 154,198 filed May 29, 1980, now abandoned.

The present invention relates to a group of novel compounds which are useful in the treatment of CNS disorders, such as epilepsy, to pharmaceutical compositions containing them, and to methods for their preparation.

U.K. Pat. No. 759,014 discloses compounds of the formula (I):

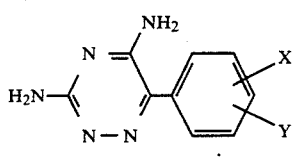

wherein X and Y are hydrogen and/or halogen atoms, as having activity against bacterial and malarial infections in animals. This patent specifically discloses those compounds wherein X and Y are both hydrogen atoms, wherein X is a hydrogen atom and Y is a 4-chloro atom, and wherein X is a 4-chloro atom and Y is a 2-chloro and 3-chloro atom, respectively.

Rees et al, *J. Med. Chem.*, 1972 15, 859, have shown that these compounds, and in particular the 4-chlorophenyl and the 3,4-dichlorophenyl compounds are active against the malaria organism *Plasmodium berghei* in mice. However, these two compounds were also shown to be toxic at curative doses and presumably were not investigated further because of their low therapeutic ratio in this context. The 2,4-dichlorophenyl compound had only slight antimalarial activity. The therapeutic ratio of the compounds were such as to prevent their use in human medicine for the treatment or prophylaxis of malaria and they were not progressed further.

U.S. Pat. No. 3,637,688 discloses compounds of the formula (II):

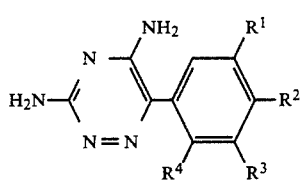

wherein $R^1$ is hydrogen or fluorine, and $R^2$, $R^3$ and $R^4$ are hydrogen, fluorine or trifluoromethyl provided that at least one of $R^1$, $R^2$, $R^3$, and $R^4$ is fluorine or trifluoromethyl, as being useful in the treatment of malaria. In the Rees article referred to above, the 4-trifluoromethylphenyl compound (II; $R^2=CF_3$, $R^1=R^3=R^4=H$) was claimed to be less toxic than the chlorophenyl compounds whilst still being active against malaria. The other fluoro and trifluoromethyl compounds referred to in the article were substantially less active than the 4-trifluoromethylphenyl compound.

Rosenburg and Bottiroli *Proc. Soc. exp. Biol.*, 1964, 115, 410, described a series of tests in which three antimalarial agents, quinacrine, chloroquine and hydroxychloroquine, were tested as anticonvulsants. Only hydroxychloroquine possessed a favourable activity profile.

It has now been discovered that a group of novel 3,5-diamino-6-(substituted phenyl)-1,2,4-triazines are active in the treatment of CNS disorders, such as psychiatric and neurological disorders, and are particularly useful as anticonvulsants, for example in the treatment of epilepsy. Furthermore, these triazines are believed to be nondepressant at likely therapeutic dose levels and therefore are advantageous as compared with depressant antiepileptics such as phenobarbitone.

Accordingly the present invention provides a compound of the formula (III):

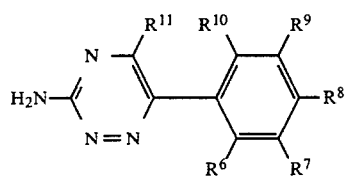

or an acid addition salt thereof, wherein $R^6$ is chlorine, bromine, iodine, $C_{1-4}$ alkyl or trifluoromethyl;

$R^7$ is hydrogen, halogen $C_{1-4}$ alkyl or trifluoromethyl or $R^6$ and $R^7$ form a $-CH=CH-CH=CH-$ group optionally substituted by a halogen atom or a $C_{1-4}$ alkyl or trifluoromethyl group, $R^8$ is hydrogen, bromine, iodine, $C_{1-4}$ alkyl or trifluoromethyl, $R^9$ is hydrogen, halogen, $C_{1-4}$ alkyl or trifluoromethyl, $R^{10}$ is hydrogen, methyl, or fluorine and $R^{11}$ is an amino, $C_{1-10}$ acylamino or di-substituted aminomethyleneamino group provided that, at most, only two of $R^7$–$R^{10}$ are other than hydrogen and that $R^7$–$R^{10}$ are not all hydrogen when $R^6$ is chlorine.

Suitably the $C_{1-4}$ alkyl group is a methyl group.

Suitably $R^6$ is a chlorine or bromine atom or a methyl or trifluoromethyl group or is linked to $R^7$ to form a $-CH=CH-CH=CH-$ group and preferably $R^6$ is a chlorine or bromine atom or linked to $R^7$ to form a $-CH=CH-CH=CH-$ group.

Preferably $R^7$ and $R^9$ are each hydrogen, chlorine or bromine atoms.

Preferably $R^8$ is a hydrogen or bromine atom.

Suitable substituents for the aminomethylene amino group are $C_{1-4}$ alkyl groups or a $-(CH_2)_2X(CH_2)_n-$ group wherein X is O, S, NH or $CH_2$ group and n is the integer 1 or 2.

Suitably $R^{11}$ is an amino, acetamido or dimethylaminomethyleneamino group and preferably $R^{11}$ is an amino group.

When three of the substituents $R^6$–$R^{10}$ are other than hydrogen, it is preferred that $R^8$ and $R^{10}$ are hydrogen and that $R^6$, $R^7$ and $R^9$ are those halogen atoms previously defined and in particular chlorine atoms.

Preferred compounds of the formula (III) include:
3,5-diamino-6-(2,3-dichlorophenyl)-1,2,4-triazine
3,5,-diamino-6-(2,5-dichlorophenyl)-1,2,4-triazine
3,5-diamino-6-(4-bromo-2-chlorophenyl)-1,2,4-triazine
3,5-diamino-6-(5-bromo-2-chlorophenyl)-1,2,4-triazine
3,5-diamino-6-(2,3,5-trichlorophenyl)-1,2,4-triazine
3,5-diamino-6-(2-chloro-6-fluorophenyl)-1,2,4-triazine
3,5-diamino-6-(2-methylphenyl)-1,2,4-triazine
3,5-diamino-6-(2-trifluoromethylphenyl)-1,2,4-triazine
3,5-diamino-6-(2-bromophenyl)-1,2,4-triazine
3,5-diamino-6-(2-iodophenyl)-1,2,4-triazine
3,5-diamino-6-(2-bromo-5-chlorophenyl)-1,2,4-triazine
3,5-diamino-6-(1-naphthyl)-1,2,4-triazine 5-acetamido-3-amino-6-(2,3-dichlorophenyl)-1,2,4-triazine 3-amino-6-(2,3-dichlorophenyl)-5-dimethylaminomethyleneamino-1,2,4-triazine 3,5-diamino-6-(2-methyl-1-naphthyl)-1,2,4-triazine.

3,5-diamino-6-(3-chloro-1-naphthyl)-1,2,4-triazine.

The present invention also provides the first practicable medical use of the compounds of the formula (III), as hereinbefore defined. Preferably this will be for the treatment of CNS disorders, and in particular epilepsy, in humans.

In a further aspect, the present invention provides pharmaceutical formulations comprising a compound of the formula (III) in admixture with a pharmaceutically acceptable carrier. Suitable acid addition salts of the compounds of formula (III) include those formed with both organic and inorganic acids. Such acid addition salts will normally be pharmaceutically acceptable. Thus, preferred salts include those formed from hydrochloric, sulphuric, citric, tartaric, phosphoric, lactic, pyruvic, acetic, succinic, oxalic, fumaric, maleic, oxaloacetic, methanesulphonic, p-toluenesulphonic and benzenesulphonic acids. The compounds of the formula (III) will be present in the compositions of the present invention in an effective unit dosage form, that is to say in an amount sufficient to be effective against CNS disorders in vivo.

The pharmaceutically acceptable carriers present in the compositions of this invention are materials recommended for the purpose of administering the medicament. These may be liquid or solid materials, which are otherwise inert or medically acceptable and are compatible with the active ingredients.

These pharmaceutical compositions may be given orally or parenterally, used as a suppository, or applied topically as an ointment, cream or powder. However, oral and parenteral administration of the compositions are preferred.

For oral administration, fine powders or granules will contain diluting, dispersing and/or surface active agents, and may be presented in a draught, in water or in a syrup, in capsules or sachets in the dry state or in non-aqueous suspension wherein suspending agents may be included, or in a suspension in water or syrup. Where desirable or necessary, flavouring, preserving, suspending, thickening or emulsifying agents can be included.

When a suspension is prepared in water according to the present invention at least one of such agents will be present.

For parenteral administration, the compounds may be presented in sterile aqueous injection solutions which may contain anti-oxidants or buffers.

As stated above, the free base or a salt thereof may be administered in its pure form unassociated with other additives in which case a capsule or sachet is the preferred carrier.

Alternatively the active compound may be presented in a pure form as an effective unit dosage, for instance, compressed as a tablet or the like.

Other compounds which may be included are, for example, medically inert ingredients, e.g. solid and liquid diluents such as lactose, starch, or calcium phosphate for tablet or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessary ingredients such as humectants, preservatives, buffers, and antioxidants which are useful as carriers in such formulations.

Tablets or other forms of presentation provided in discrete units may conveniently contain an amount of compound of the formula (III) which is effective at such dosage or as a multiple of the same, for instance, units containing 5 mg to 500 mg, usually around 10 mg to 250 mg conveniently 150 mg.

The pharmaceutical compositions of the present invention will be prepared by the admixture of a compound of the formula (III) with a pharmaceutically acceptable carrier. Conventional pharmaceutical excipients may be admixed as required.

The present invention provides a method of treatment of convulsions in mammals, and particularly epilepsy in humans by the administration of a non-toxic anticonvulsant effective amount of a compound of the formula (III) or a pharmaceutically acceptable salt, or a composition as hereinbefore defined.

As indicated above, the compounds of the formula (III) are generally useful in treating such disorders by oral administration or injection (i. p. or s. c.).

The compounds of the formula (III) are normally administered orally at a dose of from 0.1 mg/kg. to 30 mg/kg. per day for example 2 mg/kg per day. The dose range for adult humans is generally from 8 mg. to 2,400 mg/day and preferably 35 to 1,050 mg/day for example 150 mg/day. Due to the fact that the compounds of the formula (III) are extremely long acting, it may often be advantageous to administer an initial dose of 70 to 2,400 mg. the first day then a lower dose of 20 to 1,200 mg. on subsequent days.

The present invention also provides a process for the preparation of compounds of the formula (III) which comprises the cyclisation of a compound of the formula (IV):

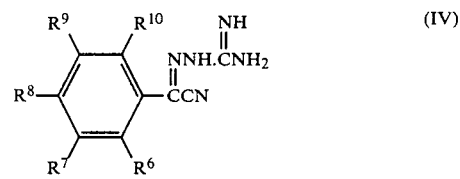

wherein $R^6$–$R^{10}$ are as hereinbefore defined; and thereafter, where desired substituting the amino group adjacent to the phenyl ring to give a group $R^{11}$ wherein $R^{11}$ is as hereinbefore defined other than amino, by conventional methods.

This cyclisation reaction is normally carried out by refluxing in an alkanol, preferably a $C_{1-4}$ alkanol such as methanol or ethanol, in the presence of a strong base such as potassium hydroxide.

The compounds of the formula (IV) are novel intermediates and as such form a further important part of the present invention.

The preparation of the compounds of the formula (IV) is analogous to that described in the literature, i.e. U.S. Pat. No. 3,637,688, for structurally related compounds.

The following examples illustrate the preparation of the compounds of the invention and their CNS activity.

EXAMPLE 1

Preparation of 3,5-diamino-6-(2,3-dichlorophenyl)-1,2,4-triazine

2,3-Dichlorobenzoic Acid

A solution of 2,3-dichloroiodobenzene (37.3 g, 0.14M) in sodium dried ether (300 mls) was added dropwise to magnesium turnings (3.65 g, 0.15 gm Atm) and a crystal of iodine with warming so as to form a Grignard reagent.

The mixture was stirred and refluxed for 2 hours then cooled and transferred dropwise, under nitrogen, into a stirred mixture of sodium dried ether (250 mls) containing solid carbon dioxide (ca. 100 g). The mixture was stirred for 2 hours, left overnight to warm to room temperature, then treated with ice (ca. 150 g) and 2N aqueous hydrochloric acid (75 mls), and the product extracted with ether (200, 100 and 50 mls). The combined ether extracts were washed with water ($2 \times 40$ mls) then repeatedly extracted with 2N aqueous sodium hydroxide (100, 50 and 50 mls). These basic solutions were combined, stirred with activated charcoal (3 g) for 10 minutes, filtered and the cooled filtrate was acidified with concentrated hydrochloric acid (25 mls) at 10° C. The resultant solid was filtered off, washed with water ($2 \times 20$ mls) and dried in vacuo. Yield 20.76 g (77.6%), m.p. 167°–169° C. (uncorrected).

2,3-Dichlorobenzoyl Chloride

A mixture of 2,3-dichlorobenzoic acid (39.4 g 0.2M) and thionyl chloride (100 mls) was heated to reflux for 2½ hours. The cooled solution was evaporated down in vacuo and distilled under nitrogen. Yield 35.5 g (85%), b.p. 146°–148° C. at 31 mm of mercury pressure.

2,3-Dichlorobenzoyl Cyanide

A mixture of cuprous cyanide (36.9 g, 0.41M), potassium iodide (68.5 g, 0.41M) and xylene (400 mls) was refluxed in an atmosphere of nitrogen under a Dean and Stark trap for 24 hours so as to remove all trace of water.

A solution of 2,3-dichlorobenzoyl chloride (35.5 g, 0.17M) in sodium dried xylene (130 mls) was added dropwise to the above mixture of dry cuprous cyanide and xylene. The resulting mixture was stirred and heated to reflux for a further 72 hours. The cooled mixture was filtered and the solid washed well with sodium dried xylene (200 mls). The filtrate and washings were combined and evaporated down in vacuo to give an oil. Yield 32 g (94%).

3,5-Diamino-6-(2,3-dichlorophenyl)-1,2,4-triazine

A solution of 2,3-dichlorobenzoyl cyanide (32 g, 0.16M) in dimethylsulphoxide (80 mls) was added dropwise to a stirred suspension of aminoguanidine bicarbonate (81.67 g, 0.6M) which had been treated with 8N aqueous nitric acid (400 mls) at a temperature of ca 25° C. The mixture was stirred for 3 hours, then left to stand at room temperature for 7 days. The cooled mixture was stirred and basified with 0.880 aqueous ammonia (400 mls) at 20° C., then stirred with ice cooling for 30 minutes, filtered and the resulting solid washed thoroughly with water and finally dried in vacuo.

The above solid was added to a 10% solution of potassium hydroxide pellets in methanol (400 mls) and the solution heated to refluxed for 1½ hours. When cool the solution was evaporated down in vacuo, treated with ice water (800 mls) then stirred for 30 minutes and filtered. The residue was dried and recrystallised from isopropanol to give 3,5-diamino-6-(2,3-dichlorophenyl)-1,2,4-triazine. Yield 6.8 g (15.6%), m.p. 216°–218° C. (uncorrected).

EXAMPLE 2

By a method analogous to that described in Example 1 the compounds listed in Tables 1 and 2 were prepared:

TABLE 1 (V)

| V;R | m.p.(uncorrected) | % Yield (from acid) |
|---|---|---|
| 2,5-Cl$_2$ | 228–230° C. | 2 |
| 2-Cl,4-Br | 223–225° C. | 6 |
| 2-Cl,5-Br | 238–240° C. | 2 |
| 2-CF$_3$ | 177–178° C. | 0.4 |
| 2-Cl,6-F | 226–228° C. | 14.5 |
| 2-Me | 181–183° C. | 25 |
| 2-Br | 204–207° C. | 34 |
| 2-I | 219–222° C. | 7 |
| 2-Br,5-Cl | 255–256° C. | 1.2 |

TABLE 2 (VI)

| VI; R | m.p.(uncorrected) | % Yield (from acid) |
|---|---|---|
| 1-I | 215–216° C. | 7.5 |
| 2-Me | 131–134° C. | 0.3 |
| 3-Cl | 285–286° C. | 1.0 |

EXAMPLE 3

Preparation of 3,5-diamino-6-(2,3,5-trichlorophenyl)-1,2,4,-triazine

2,3,5-Trichlorobenzoic Acid

Powered sodium nitrite (37.0 g, 0.54M) was added portionwise to concentrated sulphuric acid (270 ml) which was stirred under an atmosphere of nitrogen. The temperature of the mixture was not allowed to rise above 70°. Meanwhile 3-amino-2,5-dichlorobenzoic acid (100 g, 0.45M) was dissolved in hot glacial acetic acid (1,200 ml), the resultant solution was cooled rapidly to room temperature and added dropwise to the above stirred and cooled nitrous acid mixture so that the internal temperature did not rise above 30°. The solution formed after the addition was left at room temperature for 2 hours then was slowly added to a stirred solution of cuprous chloride (97 g, 0.97M) in concentrated hydrochloric acid (970 ml). The resultant mixture was stirred until the nitrogen evolution had ceased and was then left overnight. The solid was filtered off, washed well with water and dried in vacuo. Yield 90.1 g (89%) m.p. 164°–165° C. (uncorrected).

2,3,5-Trichlorobenzoyl Chloride

A mixture of 2,3,5-trichlorobenzoic acid (90 g, 0.4M) and dimethylformamide (1 ml) in thionyl chloride (200 ml) was heated to reflux for 2 hours. The cooled solution was evaporated down in vacuo and the residue distilled under nitrogen. Yield 89.2 g (90%), b.p. 158°–160° C. at the pressure of 30 mm of mercury.

2,3,5-Trichlorobenzoyl Cyanide

A mixture of cuprous cyanide (89 g, 0.9M), potassium iodide (150.5 g, 0.9M) and xylene (800 ml) was heated to reflux in an atmosphere of nitrogen under a Dean and Stark trap for 24 hours.

A solution of 2,3,5-trichlorobenzoyl chloride (89 g, 0.36M) in sodium dried xylene (100 ml) was added to the above suspension. The resulting mixture was stirred and heated to reflux for a further 72 hours. The cooled mixture was filtered and the solid was washed well with sodium dried xylene (200 ml). The filtrate and washings were combined and evaporated in vacuo to give an oil. Yield 76 g (96%).

3,5-Diamino-6-(2,3,5-trichlorophenyl)-1,2,4-triazine

A solution of 2,3,5-trichlorobenzoyl cyanide (38.5 g, 0.16M) in dimethylsulphoxide (80 ml) was added dropwise to a stirred suspension of aminoguanidine bicarbonate (65.76 g, 0.32M) which had been treated with 8N aqueous nitric acid (560 ml). The mixture was stirred for 3 hours and then was left to stand at room temperature for 21 days. The solid was filtered off, washed with water (2×100 ml) and dried in vacuo. A suspension of the dried solid in a 10% solution of potassium hydroxide pellets in methanol (320 ml) was heated to reflux for 1 hour, the mixture was cooled and evaporated down in vacuo. The residue was treated with ice/water (200 ml), the resultant solid was filtered off and dried in vacuo. This dried solid was put on top of a dry column (25 mm diameter, 200 g of MFC silica gel) and eluted with a solution of ethyl acetate/methanol/acetic acid (90:2.5:2.5). Fractions 50 to 80 (900 drops per fraction) were collected, combined and evaporated down in vacuo. The resultant solid was recrystallised from isopropanol to give 3,5-diamino-6-(2,3,5-trichlorophenyl)-1,2,4-triazine. Yield 0.77 g (1.6%), m.p. 232°–235° C. (uncorrected).

EXAMPLE 4

Preparation of 5-Acetamido-3-amino-6-(2,3-dichlorophenyl)-1,2,4-triazine

A solution of 3,5-diamino-6-(2,3-dichlorophenyl)-1,2,4-triazine (2 gm, 8 mM) and acetic anhydride (10 mls) in acetic acid (20 mls) was stirred and heated to reflux for 2 hours. The solution was then cooled and evaporated down in vacuo. The residue was treated with aqueous 0.880 ammonia (100 mls) and the resultant mixture was stirred for 2 hours. The solid was separated by filtration, dried then recrystallized from isopropanol to give 5-acetamido-3-amino-6-(2,3-dichlorophenyl)-1,2,4-triazine. Yield 1.0 gms (42%), m.p. 250°–252° C. (uncorrected).

EXAMPLE 5

Preparation of 3-Amino-6-(2,3-dichlorophenyl)-5-dimethyl aminomethyleneamino-1,2,4-triazine oxalate Dimethylformamide dimethyl acetal (1 ml) was added dropwise to a stirred mixture of 3,5-diamino-6-(2,3-dichlorophenyl)-1,2,4-triazine (1 g, 4 mM) in dry dimethylformamide (20 mls) in a nitrogen atmosphere. The mixture was stirred and heated at 120° for 2 hours, the the resultant solution was cooled and evaporated down in vacuo. The residual oil was washed once with water (20 mls) then dissolved in a solution of oxalic acid (1 gm) in methanol (20 mls). Ether (100 mls) precipitated an oil which slowly crystallized. The residue was recrystallized from aqueous isopropanol to give 3-amino-6-(2,3-dichlorophenyl)-5-dimethylaminomethyleneamino-1,2,4-triazine oxalate. Yield 0.19 gms (14%), m.p. 172°–175° C. Dec. (uncorrected).

EXAMPLE 6

Pharmacological Activity of Compounds of the Present Invention

Tables 3 and 4

The anticonvulsant activity of certain compounds of the present invention was determined by a standard maximal electroshock test, that described by L. A. Woodbury and V. D. Davenport, Arch. Int. Pharmacodyn.: 1952, 92, 97.

TABLE 3

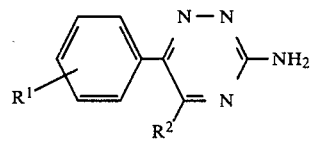
(VII)

| VII; $R^1$ | VII; R | $ED_{50}$, MES mice, mg/kg, p.o. |
|---|---|---|
| 2,3-Cl$_2$ | NH$_2$ | 2.4 |
| 2,5-Cl$_5$ | NH$_2$ | 3.3 |
| 2-Me | NH$_2$ | 15.0 |
| 2-Cl, 4-Br | NH$_2$ | 12.8 |
| 2-Cl, 5-Br | NH$_2$ | 6.0 |
| 2-CF$_3$ | NH$_2$ | 20.0 |
| 2-Cl, 6-F | NH$_2$ | 12.2 |
| 2,3,5-Cl$_3$ | NH$_2$ | 0.65 |
| 2-Br | NH$_2$ | 8.5 |
| 2-I | NH$_2$ | 11.8 |
| 2-Br, 5-Cl | NH$_2$ | 4.6 |
| 2,3-Cl$_2$ | NHCOCH$_3$ | 5 |
| 2,3-Cl$_2$ | N=CHNMe$_2$ | 5 |

TABLE 4

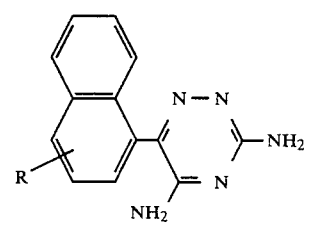
(VIII)

| VII; R | $ED_{50}$, MES mice, mg/kg, p.o. |
|---|---|
| H | 2.9 |
| 2-Me | 16.5 |

TABLE 4-continued (VIII)

[Structure: naphthalene with R substituent, connected to C(NH2)=N-N=C(NH2) triazine-like group]

| VII; R | ED$_{50}$, MES mice, mg/kg, p.o. |
|---|---|
| 3-Cl | 6.5 |

The LD$_{50}$'s (expressed in mg/kg, p.o.) of 3,5-diamino-6-(2,3-dichlorophenyl)-1,2,4-triazine and 3,5-diamino-6-(2,5-dichlorophenyl)-1,2,4,-triazine were determined in mice and rats. The LD$_{50}$ described is the dose for which 50% of the animals survive 10 days after administration of the compound.

| VII; R$^1$ | R | Mice | Rats |
|---|---|---|---|
| 2,3-Cl$_2$ | NH$_2$ | 250 | >640 |
| 2,5-Cl$_2$ | NH$_2$ | 708 | >640 |

| Tablet Formulation | | |
|---|---|---|
| 3,5-Diamino-6-(2,3-dichlorophenyl)-1,2,4-triazine | 150 mg | contents per tablet |
| Lactose | 200 mg | |
| Maize Starch | 50 mg | |
| Polyvinylpyrrolidone | 4 mg | |
| Magnesium Stearate | 4 mg | |

The drug was mixed with the lactose and starch and granulated with a solution of the polyvinylpyrrolidone in water. The resultant granules were dried, mixed with magnesium stearate and compressed to give tablets of average weight 408 mg.

We claim:

1. A compound of the formula (IV):

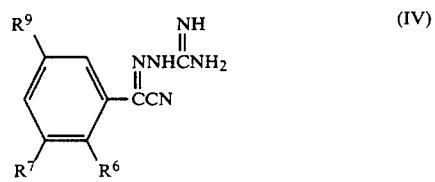

wherein R$^6$ is a chlorine or bromine atom or is linked to R$^7$ to form a CH=CH—CH=CH— group, and R$^7$ and R$^9$ are hydrogen, chlorine or bromine provided that R$^7$ and R$^9$ cannot both be hydrogen.

2. A compound of claim 1 wherein R$^6$ is chlorine and R$^7$ and R$^9$ cannot both be hydrogen.

3. A compound of claim 1 wherein R$^6$ and R$^7$ are chlorine and R$^9$ is hydrogen.

* * * * *